United States Patent [19]

Shimamune et al.

[11] Patent Number: 4,794,023
[45] Date of Patent: Dec. 27, 1988

[54] PROCESS FOR PRODUCING A CALCIUM PHOSPHATE COMPOUND COATED COMPOSITE MATERIAL

[75] Inventors: Takayuki Shimamune, Tokyo; Masashi Hosonuma; Yukiei Matsumoto, both of Kanagawa, all of Japan

[73] Assignee: Permelec Electrode Ltd., Kanagawa, Japan

[21] Appl. No.: 74,837

[22] Filed: Jul. 17, 1987

[30] Foreign Application Priority Data

Jul. 18, 1986 [JP] Japan ................................. 61-169547

[51] Int. Cl.⁴ ........................... B05D 3/02; B05D 3/12
[52] U.S. Cl. .................................. 427/350; 427/376.1; 427/380
[58] Field of Search ............ 427/295, 309, 350, 376.1, 427/380; 428/469, 472.3; 148/6.15 R

[56] References Cited

U.S. PATENT DOCUMENTS 4,108,690  8/1978  Heller .......................... 428/472.3 X
4,550,030 10/1985  Ohi et al. ...................... 427/376.1 X
4,622,078 11/1986  Optiz et al. ..................... 148/6.15 R

FOREIGN PATENT DOCUMENTS 0042783 12/1984  European Pat. Off. .
0130916  1/1985  European Pat. Off. .
1232944  5/1971  United Kingdom .

Primary Examiner—Michael Lusignan
Attorney, Agent, or Firm—Sughrue, Mion, Zinn, Macpeak, and Seas

[57] ABSTRACT

A process for producing a calcium phosphate compound coated composite material is disclosed, wherein a coating layer of a calcium phosphate compound is formed on the surface of a metal substrate by coating the surface of said metal substrate with an aqueous solution of nitric acid having hydroxyapatite dissolved therein, and then firing said coated substrate at a temperature of 300° C. or more. The composite material is useful as implants (e.g., artificial bones, dentures, and dental roots) and cements therefor.

6 Claims, No Drawings

PROCESS FOR PRODUCING A CALCIUM PHOSPHATE COMPOUND COATED COMPOSITE MATERIAL

FIELD OF THE INVENTION

The present invention relates to a process for producing a composite material formed of a metal substrate such as titanium, a titanium alloy, or a stainless steel, that is coated with a calcium phosphate compound which has a particularly good affinity for the tissues of bones or teeth. The composite material produced by the method is useful as implants (e.g., artificial bones, dentures, and dental roots) and cements therefor.

BACKGROUND OF THE INVENTION

Biocompatible implants such as artificial bones and dental roots are attracting increasing attention of researchers because if bones are fractured or teeth come out as a result of accidents or for some other reason, such implants can be joined to the remaining bone or implanted in either the lower or upper mandible so as to restore the lost bone or tooth and enable the patient to continue a comfortable life. In addition to being non-toxic to humans, such implants which are intended to be embedded in the human body must satisfy many other stringent requirements such as high strength, good machinability, non-dissolvability, appropriate values of specific gravity, and biocompatibility.

Metals such as noble metals, metal alloys such as stainless steels and ceramics such as α-alumina have heretofore been used as implants but these materials have at least one of the disadvantages of being toxic, having poor strength, having no machinability, and undergoing dissolution. In addition, they have on common problem, viz., the lack of biocompatibility.

Apatite ceramics have recently been proposed as implants that have solved the biocompatibility problem. The inorganic components of bones and teeth are calcium phosphate compounds (which are chiefly made of hydroxyapatite) and the principal components of apatite ceramics are also calcium phosphate compounds. Therefore, apatite ceramics have a very good affinity for bones and teeth and guarantee very satisfactory integration in the human body after their implantation. However, the use of such apatite ceramics is presently very limited since they have defects similar to those of the previously developed materials, such as low strength and poor machinability.

In order to solve all of the problems described above, it is strongly desired to develop metal or ceramic composite materials that are provided with biocompatibility by applying apatite coatings to the surfaces of metals or ceramics. To achieve this end, metal-to-ceramics or ceramics-to-ceramics bonding techniques are necessary but plasma spraying is the only method known to date to accomplish this type of bonding. In spite of its utility for the purpose of bonding metals to ceramics or ceramics to ceramics, the plasma spray method has the following disadvantages: it is extremely difficult to form a uniform coating over the entire surface of a material having a complex shape; it is inherently incapable of forming a coating that covers the entire surface of a porous material; it requires the use of expensive equipment; it is not capable of efficient use of costly apatite particles in coatings; and it does not always produce a strong bond between the apatite coating and the substrate.

SUMMARY OF THE INVENTION

An object, therefore, of the present invention is to provide a process for producing a composite material using titanium, a titanium alloy, a stainless steel or the like as a substrate. The composite material produced by this method has good machinability, adequate mechanical strength, and enhanced affinity for bone tissues and other parts of the human body and hence is suitable for use as artificial bones, dental roots, and other implants.

The aforementioned object of the present invention can be attained by a process for producing a calcium phosphate compound coated composite material, wherein a coating layer of a calcium phosphate compound is formed on the surface of a metal substrate by coating the surface of the metal substrate with an aqueous solution of nitric acid having hydroxyapatite dissolved therein, and by then firing the coated substrate at a temperature of 300° C. or above. The main thrust of the present invention is that a metal substrate having a coating layer of a highly crystalline calcium phosphate compound which is chiefly composed of hydroxyapatite can be readily obtained by pyrolysis.

DETAILED DESCRIPTION OF THE INVENTION

The present invention provides a process by which a calcium phosphate compound coated composite material that is suitable for use as artificial bones, dental roots, and other implants is produced. In the process of the present invention, an aqueous solution of hydroxyapatite in nitric acid is coated on a metal substrate formed of titanium, a titanium alloy, a stainless steel or the like, and the substrate is then fired to form a coating layer of a calcium phosphate compound that is chiefly composed of hydroxyapatite. In accordance with the process of the present invention, a composite material is produced that has a high degree of biocompatibility and which joins strongly to bones or other human tissues.

The term "calcium phosphate compound" as used in the present invention chiefly means hydroxyapatite; it also covers the tricalcium phosphate, calcium hydrogenphosphate and calcium dihydrogenphosphate, which would be formed as by-products when hydroxyapatite is fired in the process of the present invention, as well as other calcium-phosphate based compounds that are formed as a result of reaction between hydroxyapatite and impurities or some components of the substrate.

Examples of the metal used in the present invention include titanium, titanium alloys, and stainless steel or the like, all of which are stable in the human body. Titanium means metallic titanium and illustrative titanium alloys are those which contain such alloying elements as Ta, Nb, platinum-group metals, Al, and V. The term "stainless steel or the like" covers not only stainless steel such as SUS 304, SUS 310, and SUS 316 specified in the JIS (the Japanese Industrial Standards) but also other corrosion-resistant alloys such as Co-Cr alloys that are suitable for implantation in the human body. The metal substrate which is made of one of these metallic materials may have a smooth surface as in the form of a sheet or rod, or a porous surface as in a sponge. The substrate may also be in the form of an expanded metal screen or a porous sheet. The above-mentioned metallic materials are used as the substrate because they have a satisfactorily high mechanical strength as compared with sintered ceramics or glass and because they are readily machinable. If desired, the substrate may be provided with improved affinity for the calcium phosphate compounds by cleaning its surface of any impurities by means of washing with water, acids, ultrasonic waves, steam, or some other appropriate cleaning media. Additionally, the surface of the substrate may be roughened by blasting and/or etching so as to provide enhanced affinity for the calcium phosphate compounds and to activate the surface of the substrate as well. Etching may be accomplished not only by chemical methods, but by physical methods such as sputtering.

After an appropriate surface treatment has been performed in the manner described above, the surface of the substrate is coated with an aqueous solution of nitric acid, in which hydroxyapatite is dissolved or which is preferably saturated with hydroxyapatite, by any conventional method such as dipping, spraying, or using a brush or a coater. The coated substrate is then fired to produce a coating layer that has a strong bond to the substrate metal.

It is desirable to use a concentrated aqueous solution of nitric acid since the solubility of hydroxyapatite increases with increasing concentration of nitric acid. About 1.5 g of hydroxyapatite dissolves in 10 ml of an aqueous solution of 12% nitric acid and about 3 g of hydroxyapatite dissolves in 10 ml of a 25% solution. If the concentration of nitric acid is 60%, 7 g or more of the hydroxyapatite dissolves in 10 ml of the solution to produce a highly viscous solution. An aqueous solution of less than 10% nitric acid is capable of dissolving hydroxyapatite but only in such a small amount that repeated application of the aqueous solution of nitric acid has to be performed in order to produce a coating layer of a calcium phosphate compound having a desired thickness. In order to ensure an efficient coating operation, the concentration of nitric acid in the coating solution is desirably set to at least 10% so that the required number of coating and firing cycles can be decreased. The nitric acid solution is desirably saturated with hydroxyapatite for attaining the following two purposes: maximizing the deposit of coating that can be formed by a single firing; and producing a high degree of crystallinity in the coating layer.

In the present invention, hydroxyapatite is selected as the compound to be dissolved in the coating solution for application to the substrate and it is dissolved in an aqueous solution of nitric acid; this is in order to produce a coating layer that is chiefly composed of highly biocompatible and crystalline hydroxyapatite and which has a strong bond to the metal substrate. Other reasons for using an aqueous solution of nitric acid as a solvent for the coating solution are as follows: nitric acid has a high solubility for hydroxyapatite; and the oxidizing power of nitric acid passivates the surface of the metal substrate and thereby minimizes possible corrosion of the substrate so as to form a coating of a calcium phosphate compound that has a strong bond to the substrate.

When the aqueous solution of hydroxyapatite in nitric acid that has been coated on the metal substrate is fired, the hydroxyapatite will be precipitated on the surface of the substrate in the form of a calcium phosphate compound that is chiefly composed of hydroxyapatite. An optimum value of the temperature for firing varies with the concentration of nitric acid, and the higher the concentration of nitric acid, the higher the temperature that is optimum for the purpose of firing the substrate. A preferable range of firing temperatures is from 300° to 800° C. If the firing temperature is less than 300° C., the resulting coating layer of a calcium phosphate compound has insufficient strength and affords an inadequate bond to the substrate. If the firing temperature exceeds 800° C., the surface of the metal substrate will undergo too rapid an oxidation to produce a strongly adhering coating of a calcium phosphate compound. Optimum firing temperatures range from 350° to 500° C. if the coating solution has a nitric acid concentration of 10%, and from 450° to 700° C. if the nitric acid concentration is 60%.

The metal substrate to which the coating solution has been applied may be fired in an oxidizing atmosphere typified by air but, in order to prevent thermal oxidation of the substrate and to provide a composite material having a better finished appearance, the firing of the substrate is preferably effected in an inert atmosphere typified by argon gas, or in vacuum. Even if firing is carried out under such inert conditions, decomposition gases will be evolved during heating and cause slight oxidation of the surface of the substrate in uncoated areas. However, any oxide film that has formed in such areas can be readily removed by chemical polishing or other appropriate methods.

By the procedures described above, a coating layer of a calcium phosphate compound which is chiefly composed of hydroxyapatite can be formed on the surface of the metal substrate. If the thickness of coating that is attained by a single cycle of coating and firing operations is insufficient, this cycle may be repeated until the desired thickness is obtained.

In the process of the present invention, the coating solution is which hydroxyapatite is dissolved is applied to the surface of a metal substrate, which then is fired to have a hydroxyapatite-based calcium phosphate compound precipitated from the coating solution. Therefore, the process of the present invention is applicable to substrates of any shape, and a uniform coating layer of the calcium phosphate compound can be formed on the entire surface of the substrate even if it is porous.

The following examples are provided for the purpose of further illustrating the present invention but are in no way to be taken as limiting. Unless otherwise specified, all percents, ratios, etc. are by weight.

EXAMPLE 1

About 3 g of a hydroxyapatite ($Ca_{10}(PO_4)_6(OH)_2$) powder was slowly added to 10 g of an aqueous solution of 25% nitric acid under stirring to prepare a coating solution which was saturated with hydroxyapatite.

Specimens measuring 40 mm long and 20 mm wide were cut from a rolled sheet 1 mm thick of stainless steel SUS 316L and their surfaces were roughened by blasting with a #70 corundum grit. The specimens were then etched by immersion in an aqueous solution of 30% $FeCl_3$ at 25° C. for 4 minutes.

Some of the etched specimens were coated on one side with the above-described coating solution and immediately dried at 60° C. for 20 minutes in an argon stream, followed by firing at 500° C. for 10 minutes in an argon atmosphere.

When two cycles of the coating and firing operations were run, a white coating layer formed over the surface of each of the treated specimens. Identification by X-ray diffraction produced a strong diffraction peak that was ascribed to hydroxyapatite and the resulting coating layer was found to be composed of highly crystalline hydroxyapatite.

The remainder of the stainless steel specimens was subjected to the same treatment as described above except that the argon stream was replaced by air. In this case, unwanted coloration occurred owing to oxidation of the stainless steel substrate, and 16 cycles of coating and firing operations had to be run in order to attain satisfactory whiteness for the coating layer. Analysis by X-ray diffraction showed that this coating layer was also composed of highly crystalline hydroxyapatite.

EXAMPLE 2

Hydroxyapatite powders were slowly added to aqueous solutions of varying concentrations of nitric acid at 25° C. under stirring so as to prepare four coating solutions which were saturated with hydroxyapatite as shown in Table 1.

Specimens measuring 40 mm long and 20 mm wide were cut from a rolled sheet 1 mm thick of stainless steel SUS 316L and their surfaces were roughened by blasting with a #70 corundum grit. The specimens were then cleaned by immersion in an aqueous solution of 30% $FeCl_3$ at 25° C. for 4 minutes.

TABLE 1

| Coating solution No. | $HNO_3$ concentration | Hydroxyapatite in 10 g of aqueous solution of $HNO_3$ |
| --- | --- | --- |
| 1 | 5% | ca. 0.6 g |
| 2 | 12% | ca. 1.5 g |
| 3 | 25% | ca. 3.0 g |
| 4 | 35% | ca. 4.0 g |

Each of the stainless steel specimens was coated on one side with one of the four coating solutions and immediately dried at 60° C. for 20 minutes in an argon stream, followed by firing in an argon atmosphere. Different temperatures were used to fire specimens coated with different coating solutions. The number of cycles of coating and firing operations that had to be performed in order to attain coating layers having a satisfactory degree of whiteness also differed for each coating solution. The results are shown in Table 2.

TABLE 2

| Coating solution No. | Firing temperature (°C.) | Number of coating and firing cycles |
| --- | --- | --- |
| 1 | 350–420 | 14 |
| 2 | 400–450 | 7 |
| 3 | 470–500 | 3 |
| 4 | 500–600 | 2 |

It is clear that as the concentration of nitric acid in the coating solutions increased, the temperatures required for pyrolysis increased, but the number of coating and firing cycles that had to be run decreased.

EXAMPLE 3

A coating solution was prepared by slowly adding about 4 g of a hydroxyapatite powder to a well stirred aqueous solution (10 g) of 35% nitric acid as it was held at 25° C.

Specimens measuring 40 mm long and 20 mm wide were cut from a rolled titanium (JIS Type 1) sheet 1 mm thick and their surfaces were roughened by blasting with a #80 steel shot, followed by immersing in an aqueous solution of 25% nitric acid at 90° C. for 30 minutes. An intimate mixture of 5 g of a powder of titanium spheres (particle size: 250–350 $\mu$m), 0.05 g of a titanium powder (particle size: 10 $\mu$m or less) and 2 ml of an aqueous solution of 5% polyvinyl alcohol (polymerization degree: 500) was coated on the treated specimens in such a manner that 2 or 3 layers of spherical titanium powder would align on each substrate. The coated specimens were dried at 60° C. for 20 minutes, heated to 1,250° C. at a rate of 2° C./min and at a pressure of no higher than $1 \times 10^{-5}$ mmHg, held at 1,250° C. for 30 minutes, and furnace-cooled.

The resulting titanium sheets having a porous surface were immersed with an aqueous solution of 15% nitric acid at 60° C. for 1 hour, thoroughly washed with water, and dried. After being submerged in the above-described coating solution, the titanium sheets were immediately spun at 1,000 rpm to remove excess solution by centrifugation. Immediately thereafter, the titanium sheets were dried at 60° C. for 1 hour in an argon stream, and fired at 550° C. for 10 minutes in an argon atmosphere. When one more cycle of coating and firing operations was conducted, a white coating layer formed over the surface of each specimen. Identification by X-ray analysis showed that this coating layer was formed of highly crystalline hydroxyapatite. Observation of a cross section of each specimen with an electron microscope showed that although its surface was uniformly covered with the coating layer of hydroxyapatite, individual titanium spheres in the substrate were not bridged by the hydroxyapatite layer and voids having a maximum diameter of about 200 $\mu$m were left between adjacent titanium spheres.

The advantages offered by the present invention are summarized below.

First, the composite material produced by the process of the present invention uses corrosion-resistant titanium, titanium alloys, or stainless steels as the substrate, so that is can be used as an artificial bone or dental root that is not only harmless to the human body but also stable with the least possibility of dissolution. In addition, this composite material has satisfactory mechanical strength and can be readily machined.

Secondly, the composite material produced by the present invention has a coating of hydroxyapatite-based calcium phosphate compound formed on the surface of the metal substrate so that it has sufficient biocompatibility to be bonded to bones and other tissues of the human body in an easy and yet reliable manner.

Thirdly, in the process of the present invention, a calcium phosphate compound that is chiefly composed of hydroxyapatite is allowed to precipitate from an aqueous solution of hydroxyapatite in nitric acid. Therefore, a uniform coating layer of calcium phosphate compound can be formed on the substrate no matter what shape it may have. In addition, the calcium phosphate compound can be efficiently used to form a highly crystalline and therefore high-quality coating on the substrate.

Fourthly, the coating layer itself has satisfactory strength since it is chiefly made of highly crystalline hydroxyapatite. This feature, coupled with the enhanced biocompatibility of hydroxyapatite, leads to a remarkable improvement in the function of the composite material as an implant intended to be used in the human body.

While the invention has been described in detail and with reference to specific embodiments thereof, it will be apparent to one skilled in the art that various changes and modifications can be made therein without departing from the spirit and scope thereof.

What is claimed is:

1. A process for producing a calcium phosphate compound coated composite material, comprising coating the surface of said metal substrate with an aqueous solution of nitric acid having hydroxyapatite dissolved therein to form a coating layer of a calcium phosphate compound on the surface of a metal substrate, and then firing said coated substrated at a temperature of 300° C. or more.

2. A process according to claim 1, wherein said metal substrate is made of titanium or an alloy thereof.

3. A process according to claim 1, wherein said metal substrate is made of stainless steel or cobalt-chromium alloy.

4. A process according to claim 1, wherein said aqueous solution of nitric acid has a nitric acid concentration of at least 10%.

5. A process according to claim 1, wherein the substrate is fired in an inert atmosphere or in vacuum.

6. A process according to claim 1, wherein the cycle of coating and firing operations is run more than once.

* * * * *